US009526345B2

(12) United States Patent
Tucker et al.

(10) Patent No.: US 9,526,345 B2
(45) Date of Patent: Dec. 27, 2016

(54) BOTULINUM TOXIN ASSAY WITH IMPROVED SENSITIVITY

(71) Applicant: BIOMADISON, INC., Del Mar, CA (US)

(72) Inventors: Ward C. Tucker, Monona, WI (US); Tim Piazza, McFarland, WI (US)

(73) Assignee: BIOMADISON, INC., Del Mar, CA (US)

( * ) Notice: Subject to any disclaimer, the term of this patent is extended or adjusted under 35 U.S.C. 154(b) by 146 days.

(21) Appl. No.: 14/455,786

(22) Filed: Aug. 8, 2014

(65) Prior Publication Data

US 2015/0159193 A1    Jun. 11, 2015

Related U.S. Application Data

(60) Provisional application No. 61/864,436, filed on Aug. 9, 2013.

(51) Int. Cl.

| C12Q 1/37 | (2006.01) |
| A47C 15/00 | (2006.01) |
| G01N 21/64 | (2006.01) |
| G01N 33/569 | (2006.01) |
| C12Q 1/68 | (2006.01) |

(52) U.S. Cl.
CPC .............. *A47C 15/006* (2013.01); *C12Q 1/37* (2013.01); *C12Q 1/6897* (2013.01); *G01N 21/6408* (2013.01); *G01N 21/6428* (2013.01); *G01N 33/56911* (2013.01); *G01N 2333/33* (2013.01)

(58) Field of Classification Search
USPC .................. 435/23, 325, 326, 6.13
See application file for complete search history.

(56) References Cited

U.S. PATENT DOCUMENTS

| 7,183,066 B2 | 2/2007 | Fernandez-Salas |
| 7,208,285 B2 | 4/2007 | Steward |
| 7,449,299 B2 * | 11/2008 | Bauer ............... B82Y 15/00 435/17 |
| 7,598,027 B2 * | 10/2009 | Fernandez-Salas ............... G01N 33/56911 435/23 |
| 8,137,924 B2 * | 3/2012 | Chapman ......... C07K 14/43595 435/7.32 |
| 8,497,081 B2 * | 7/2013 | Fernandez-Salas ............... G01N 33/5014 435/7.2 |

(Continued)

FOREIGN PATENT DOCUMENTS

WO    2014060373 A1    4/2014

OTHER PUBLICATIONS

Pires-Alves, Melissa et al, Toxicon, Mar. 15, 2009, vol. 53(4), pp. 392-399, Tandem Fluorescent Protiens as Enhanced FRET based substrates for Botulinum Neurotoxin Activity.*

(Continued)

*Primary Examiner* — Albert Navarro
*Assistant Examiner* — Ginny Portner
(74) *Attorney, Agent, or Firm* — Fish & Tsang, LLP

(57) ABSTRACT

Methods and compositions are provided where a transfected cell that produces a hybrid protein with a reporter-containing portion and a *botulinum* toxin cleavage site is contacted with a *botulinum* toxin at elevated temperatures and/or in media having a reduced sodium concentration. Kits that include such media and a *botulinum* toxin are also described.

12 Claims, 12 Drawing Sheets

(56) References Cited

U.S. PATENT DOCUMENTS

| | | | | |
|---|---|---|---|---|
| 8,623,999 | B2* | 1/2014 | Steward | C07K 14/33 435/252.3 |
| 8,778,623 | B2* | 7/2014 | Johnson | C12Q 1/37 435/326 |
| 8,940,482 | B1* | 1/2015 | Oyler | C12Q 1/37 435/6.1 |
| 8,969,016 | B2* | 3/2015 | Fish | C12Q 1/37 422/430 |
| 8,999,649 | B2* | 4/2015 | Chapman | C07K 14/43595 435/6.15 |
| 9,217,172 | B2* | 12/2015 | Johnson | G01N 33/5073 |
| 9,303,284 | B2* | 4/2016 | Fish | C12Q 1/37 |
| 9,303,285 | B2* | 4/2016 | Piazza | G01N 33/582 |
| 2004/0191887 | A1 | 9/2004 | Chapman | |
| 2006/0134722 | A1* | 6/2006 | Chapman | C07K 14/43595 435/23 |
| 2008/0274480 | A1* | 11/2008 | Atassi | G01N 33/56911 435/7.21 |
| 2009/0263836 | A1* | 10/2009 | Fernandez-Salas | G01N 33/5014 435/7.32 |
| 2011/0033866 | A1* | 2/2011 | Fish | C12Q 1/37 435/7.1 |
| 2012/0309039 | A1* | 12/2012 | Atapattu | G01N 33/582 435/23 |

OTHER PUBLICATIONS

Apr. 10, 2011, BioSentinel Parmaceuticals, pp. 1-4, letter for Submission of BoTest®, BoTest® Matrix and BoCell® Botulinum Neurotoxin Activity assays for cross-laboratory validation studies by ICCVAM and NICEATM.*

Pellett, Sabine, Current Topics in Microbiology and IMmunology, 2013, vol. 364, pp. 257-285, Progress in Cell Based Assays for Botulinum Neurotoxin Detection.*

A Cell Based Assay for Botulinum Neurotoxin Detection and Development, pp. 1-2, Award year 2011.*

Kukreja, Roshan et al, The Journal of Biological Chemistry, vol. 280(47) pp. 39346-39352, Nov. 25, 2005, Biologically Active Novel Conformational State of Botulinum, the Most Poisonous Poison.*

* cited by examiner

Trial 1

| | EC$_{50}$(pM) |
|---|---|
| ● 35°C | 2.72 |
| ◆ 37°C | 31.00 |
| ▼ 39°C | 0.14 |

Trial 2

| | EC$_{50}$(pM) |
|---|---|
| ● 35°C | 2.12 |
| ◆ 37°C | 0.75 |
| ▼ 39°C | 0.15 |

Trial 3

| | EC$_{50}$(pM) |
|---|---|
| ● 37°C | 1.58 |
| ◆ 39°C | 0.47 |
| ▼ 41°C | 0.27 |

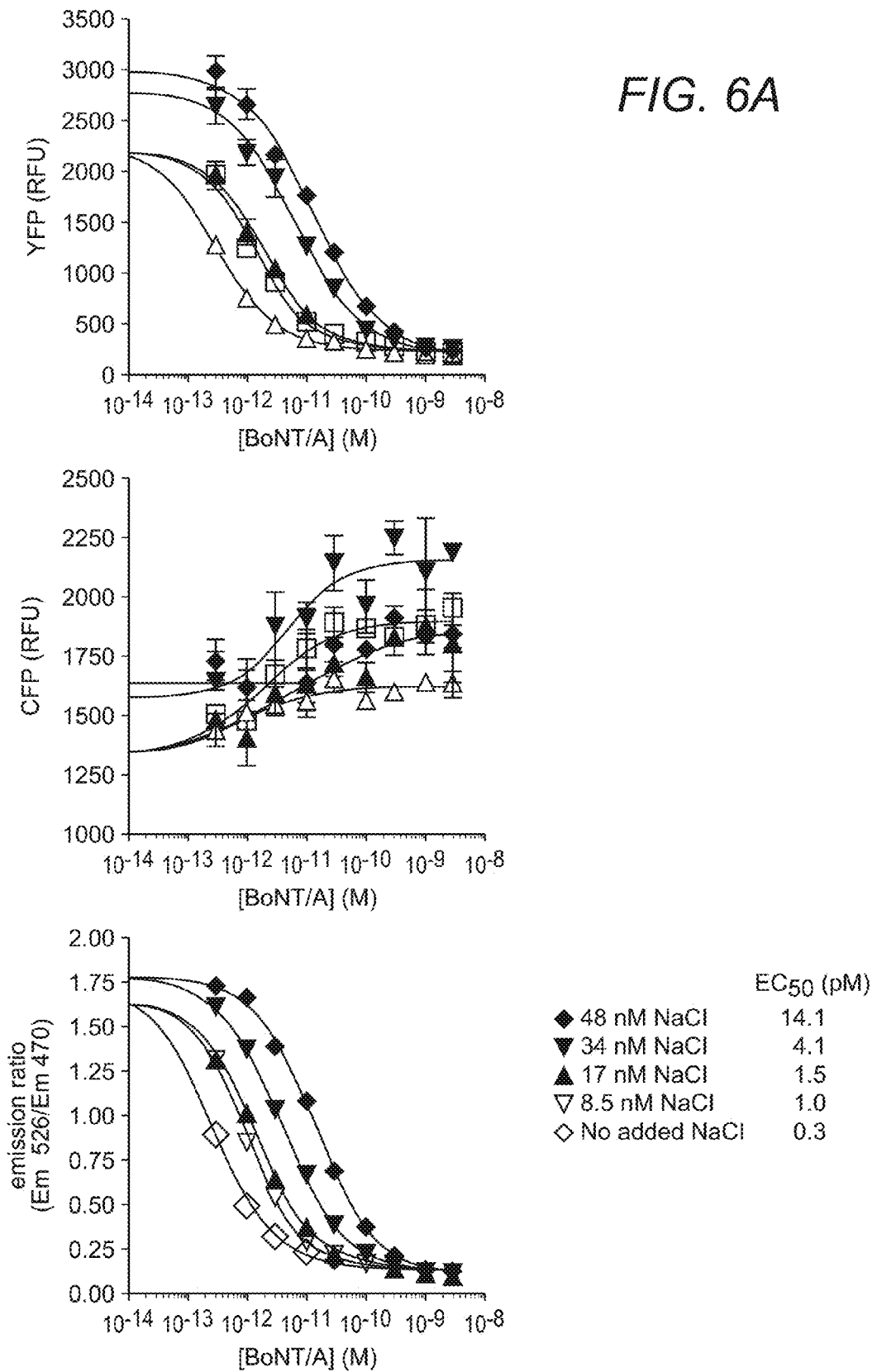

| | EC$_{50}$(pM) |
|---|---|
| Media A preincubation, Media C wash and BoNT | 9.30 |
| media C preincubation, wash, and BoNT | 0.86 |
| Media A preincubation, Media C wash, Media B BoNT | 0.94 |
| Media A preincubation, Media B wash and BoNT | 0.78 |

FIG. 9A

| | EC$_{50}$(pM) |
|---|---|
| 70% Neurobasal | 23.7 |
| 18.3 mM NaHCO3 | 12.0 |
| 13.1 mM NaHCO3 | 5.9 |
| 6.5 mM NaHCO3 | 6.2 |
| 3.3 mM NaHCO3 | 6.1 |
| 0 mM NaHCO3 | 4.2 |

| | EC$_{50}$(pM) |
|---|---|
| ● 70% NaCl Custom | 13.7 |
| ◆ 25% NaCl Custom | 1.0 |
| ○ 70% KCl Custom | 2.5 |
| ◇ 25% KCl Custom | 1.4 |

FIG. 11

| | EC$_{50}$(pM) |
|---|---|
| ● 70% Neurobasal | 28.4 |
| ○ 70% Custom 0mM NaCl | 0.5 |
| ◆ 96.6 mM Sucrose | 2.8 |
| ◇ 34.4 mM Sucrose | 0.8 |
| ▼ 96.6 mM TMAO | 0.3 |
| ▽ 34.4 mM TMAO | 0.3 |

FIG. 12A

| | EC$_{50}$(pM) |
|---|---|
| ● BoNT/A | 0.3 |
| ○ BoNT/A + HcR/A | 144 |

FIG. 12B

| | EC$_{50}$(pM) |
|---|---|
| ● Holotoxin | 0.2 |
| ○ Lc/A | — |

BOTULINUM TOXIN ASSAY WITH IMPROVED SENSITIVITY

This application claims the benefit of priority to U.S. Provisional Application No. 61/864,436 filed on Aug. 9, 2013. This and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

FIELD OF THE INVENTION

The field of the invention is protease assays related to *botulinum* toxins.

BACKGROUND

*Botulinum* neurotoxins (BoNTs) are produced by *Clostridium botulinum*, and are among the most potent toxins known. These toxins are a well-recognized source of food poisoning, often resulting in serious harm or even death of the victims. There are seven structurally related *botulinum* neurotoxins or serotypes (BoNT/A-G), each of which is composed of a heavy chain (~100 KD) and a light chain (~50 KD). The heavy chain mediates toxin entry into a target cell through receptor-mediated endocytosis. Once internalized, the light chain is translocated from the endosomal vesicle lumen into the cytosol, and acts as a zinc-dependent protease to cleave proteins that mediate vesicle-target membrane fusion ("substrate proteins").

These BoNT substrate proteins include plasma membrane protein syntaxin, peripheral membrane protein SNAP-25, and a vesicle membrane protein synaptobrevin (Syb). These proteins are collectively referred to as the SNARE (soluble N-ethylmaleimide-sensitive factor attachment protein receptor) proteins. Cleavage of SNARE proteins blocks vesicle fusion with plasma membrane and abolishes neurotransmitter release at neuromuscular junction. Among the SNARE proteins, syntaxin and SNAP-25 usually reside on the target membrane and are thus referred to as t-SNAREs, while synaptobrevin is found exclusively with synaptic vesicles within the synapse and is called v-SNARE. Together, these three proteins form a complex that is thought to be the minimal machinery to mediate the fusion between vesicle membrane and plasma membrane. BoNT/A, E, and C cleave SNAP-25, BoNT/B, D, F, G cleave synaptobrevin (Syb), at single but different sites. BoNT/C also cleaves syntaxin in addition to SNAP-25.

Due to their threat as a source of food poisoning, and as bioterrorism weapons, there is a need to sensitively and speedily detect BoNTs. Currently, the most sensitive method to detect toxins is to perform toxicity assay in mice. Such methods, however, entail considerable expense and are subject to regulations related to animal testing.

As a result, there is a growing interest in developing alternatives to animal-based methods for BoNT characterization. An attractive alternative is the use of cell-based assays, which maintain the receptor-based internalization and subsequent cleavage of the BoNT molecule that is generally absent from conventional in vitro assays. Such cell-based assays utilize cells that express constructs that are responsive to the BoNT, in some instances utilizing Förster resonance energy transfer (FRET) and in other instances utilizing non-FRET methods to provide fluorescence useful for the detection and characterization of BoNTs. Examples can be found in United States Patent Application No. 2004/0,191,887 (to Chapman), United States Patent Application No. 2006/0,134,722 (to Chapman), U.S. Pat. No. 7,208,285 (to Steward), U.S. Pat. No. 7,183,066 (to Fernandez-Salas), and United States Patent Application No. 2011/0,033,866 (to Atapattu), each of which is incorporated herein by reference in their entirety. For some applications, however, the sensitivity of such cell-based methods can be lacking. For example, United States Patent Application No. 2006/0,134,722 (to Chapman) discloses that EC50 value of cell based FRET assay to detect BoNTs is in the ≥10 pM range.

International Patent Application No. WO 2014/060373 (to Eisele) reported enhancement of the sensitivity of cells to intoxication with *botulinum* toxin by allowing certain tumor cells that had been primed for differentiation into neuronal cells to differentiate in a low osmolarity differentiation media for several days to several weeks prior to exposure to the toxin. Sensitivity was determined by lysis of the treated cells followed by a Western blot method directed towards SNAP-25. The utility of Western blotting as a quantitative method is considered debatable, however, and no data demonstrating the statistical significance of the reported differences was provided.

Although some success has been demonstrated in applying FRET assays to detection of BoNTs, the sensitivity of FRET assay to BoNTs has been still undesirable for many purposes. As few as 40 nanograms of BoNT is a lethal dose for most people, and samples suspected to contain BoNTs are often are prior to application to the test process. It is, therefore, strongly desirable to have methods that detect low concentrations of BoNT.

SUMMARY OF THE INVENTION

Methods and compositions are disclosed that provide for increased sensitivity in cell-based assays for *botulinum* toxins. Cells are provided that express a reporting construct that is responsive to *botulinum* toxin. Temperature and media compositions are identified that provide increased sensitivity of the transfected cell response to *botulinum* toxin relative to conventional temperatures and media compositions.

One embodiment of the inventive concept is a method of increasing the sensitivity of cell-based detection of a *botulinum* toxin (for example, BoNT/A) by providing a transfected cell that expresses a hybrid protein, where the hybrid protein includes a reporter-containing portion (for example, at or near a terminus of the hybrid protein) and a cleavage site, where the cleavage site is cleaved by a *botulinum* toxin to release the reporter-containing portion (for example, a portion containing a fluorophore) from the remainder of the hybrid protein. Suitable cells include neuronal, neuroendocrine tumor, hybrid, and stem cells. In this process transfected cell is exposed to a temperature of 38° C. to 41° C. or 38.5° C. to 39.5° C. during exposure to the *botulinum* toxin, resulting in at least a two-fold increase in the sensitivity of the cell to *botulinum* toxin relative to the cell's sensitivity to *botulinum* toxin at 37° C. In some embodiments the sensitivity enhancement is selective for BoNT/A. Alternatively, in some embodiments the transfected cells are exposed to a pre-toxin temperature (for example, 38° C. to 41° C. or 38.5° C. to 39.5° C.) prior to exposure to *botulinum* toxin. In some embodiments the hybrid protein includes a second fluorophore in addition to a fluorophore of the reporter-containing portion, and such a second fluorophore can be located at a different terminus of the hybrid protein than that of the reporter-containing portion. In preferred embodiments such fluorophores are arranged so that no significant (i.e. ≤5%) energy transfer via Förster resonance energy occurs between the fluorophores.

Another embodiment of the inventive concept is a method of increasing the sensitivity of cell-based detection of a *botulinum* toxin by providing, in a first media a sodium concentration greater than 65 mM, a transfected cell that expresses a hybrid protein, where the hybrid protein includes a reporter-containing portion (for example, at or near a terminus of the hybrid protein) and a cleavage site, where the cleavage site is cleaved by a *botulinum* toxin to release the reporter-containing portion (for example, a portion containing a fluorophore) from the remainder of the hybrid protein. The cell is then transferred to a second media having a sodium concentration of less than 50 mM (for example, less than 45 mM) and is contacted with a *botulinum* toxin in the second media. In some embodiments the transfected cell is exposed to the *botulinum* toxin upon transfer to the second media (i.e. without pre-incubation in the second media). Thereafter a signal is obtained from the reporter-containing portion of the hybrid protein. In such a method the sensitivity of the transfected cell to *botulinum* toxin can be increased by a factor of 10 or more relative to a method where the cell is maintained in and exposed to *botulinum* toxin in the first media (i.e. a media with a sodium concentration of at least 65 mM). The sodium concentration in the second media can be reduced by a reduction in the sodium content of a neurobasal media, for example by reducing the concentration of sodium chloride and/or sodium bicarbonate. In some embodiments the first media, the second media, or both can be of physiological osmotic strength. In other embodiments, the first media, the second media, or both can have an osmotic strength that is less than that of physiological osmotic strength, for example 250 mOsm or less.

Still another embodiment of the inventive concept is a kit for improving the sensitivity of a cell-based assay for a *botulinum* toxin, where the kit includes a set of standards containing *botulinum* toxin supplied at two or more different concentrations in sensitivity enhancing media as described above. Such a kit can include two or more preparations containing non-zero concentrations of *botulinum* toxin in such media, and in some embodiments can include a blank or zero (i.e. media-only) preparation. Such a kit can be used to prepare and/or verify dose/response curves useful for quantitation of *botulinum* toxin in a sample (for example, in the preparation of a calibration curve or verification of assay performance relative to a calibration curve stored in memory).

BRIEF DESCRIPTION OF THE DRAWINGS

FIGS. 1A, 1B, and 1C show the response of transfected cells to *botulinum* toxin and fragments thereof at different temperatures. FIG. 1A shows the response of transfected cells to *botulinum* holotoxin at different temperatures. FIG. 1B shows the response of transfected cells to *botulinum* holotoxin or to the light chain of *botulinum* toxin at different temperatures. FIG. 1C shows the response of transfected cells to *botulinum* holotoxin in the presence of the heavy chain of *botulinum* toxin at different temperatures.

FIG. 3A shows the response of transfected cells in a media having an ionic strength of 270 mM. FIG. 3B shows the response of transfected cells to *Botulinum* toxin in a media having an ionic strength of 250 mM.

FIGS. 4A and 4B show the effects of elevated temperatures on the response of transfected cells to *botulinum* toxin and in the absence of *botulinum* toxin. FIG. 4A shows the response of transfected cells to *botulinum* toxin at temperatures up to 41° C. FIG. 4B shows brightfield and fluorescence photomicrographs of the response of transfected cells to temperatures of up to 41° C. in the absence of *botulinum* toxin.

FIGS. 6A to 6B show the effect of media with reduced sodium concentration on cell-based assays for *botulinum* toxin. FIG. 6A shows the effect of the use of proprietary media with different concentrations of added NaCl. FIG. 6B shows photomicrographs of transfected cells exposed to custom culture media containing different concentrations of NaCl.

FIG. 7 shows the response of transfected cells to *botulinum* toxin in media with different sodium concentrations and at different time points following exposure to the toxin.

FIGS. 8A, 8B, and 8C show the result of exposure of transfected cells to *botulinum* toxin in media with reduced sodium content for different lengths of time prior to the restoration of normal sodium concentrations. FIG. 8A shows the effects when transfected cell are cultured in conventional media prior to exposure to *botulinum* toxin. FIG. 8B shows the effects when the transfected cells are cultured in low sodium content media prior to exposure to *botulinum* toxin.

FIGS. 9A and 9B show the result of reducing sodium bicarbonate concentration in media used in cell-based assays for *botulinum* toxin. FIG. 8A shows dose/response curves in media with different concentration of sodium bicarbonate. FIG. 8B shows the effect on EC50s calculated from such dose/response curves as a function of sodium bicarbonate concentration in the media. FIG. 8C shows the effect of pre-incubation with either conventional media or media with reduced sodium content prior to the performance of a cell-based assay for *botulinum* toxin in low sodium content media.

FIG. 10 shows the effect of replacing sodium with potassium in custom media used in cell-based assays for *botulinum* toxin, and in the reduction of sodium and potassium concentrations in those media.

FIG. 11 shows the effect of increasing the osmolarity of low sodium content media used in cell-based assays for *botulinum* toxin.

FIGS. 12A and 12B show the effects of *botulinum* toxin fragments and intact *botulinum* holotoxin on transfected cells in media with reduced sodium content. FIG. 12A shows the effect of adding recombinant *botulinum* toxin heavy chain to the transfected cells prior to exposure to the holotoxin. FIG. 12B shows the effect of adding recombinant *botulinum* toxin light chains to the transfected cells and the effect of adding the intact *botulinum* holotoxin to the transfected cells.

DETAILED DESCRIPTION

Figure 1B:
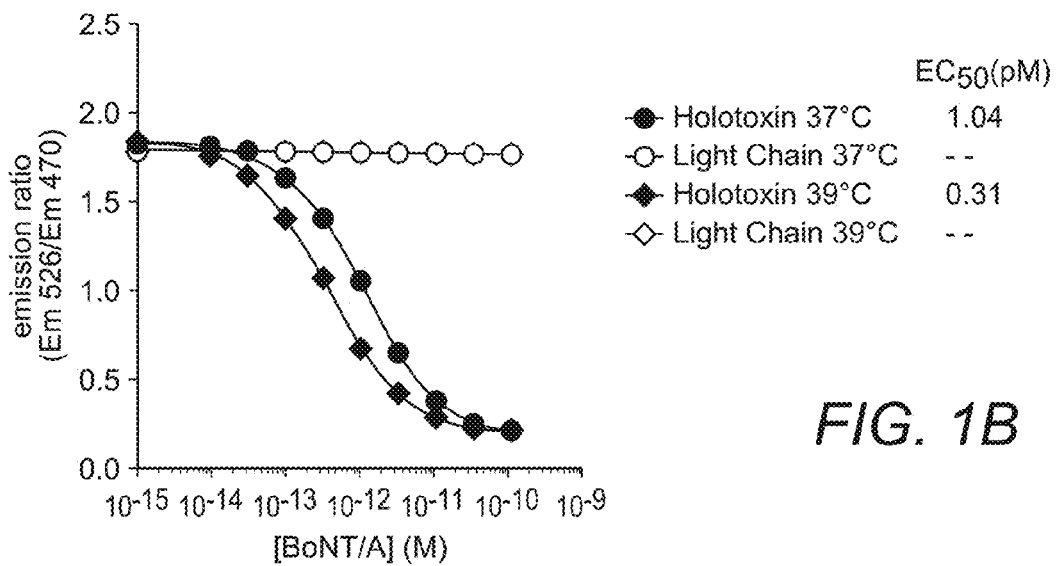

The inventive subject matter provides methods in which the sodium ion concentration of cell culture media utilized in a cell-based *botulinum* toxin assay and/or the temperature at which the cell-based *botulinum* assay is performed is used to provide *botulinum* assays with enhanced sensitivity. Surprisingly, the inventors have found that reduction of sodium ion concentration in the cell culture media enhances sensitivity of *botulinum* toxin in an ion and *botulinum* toxin-specific manner. The inventors also identified a narrow range of temperatures over which the sensitivity of such assays, as defined by dose/response curves, is dramatically enhanced.

The inventive subject matter provides methods for improving the sensitivity of cell-based methods for detecting the presence of a *botulinum* toxin (BoNT). A variety of assays for *botulinum* toxins that utilize transfected cells expressing detecting constructs cleavable by these proteases have been developed. In cell-based assays, specific binding of the heavy chain of a *botulinum* toxin by cell surface receptors and followed by specific cleavage of a construct that includes a *botulinum* toxin-specific cleavage site by the light chain of the *botulinum* toxin and subsequent release of an indicator moiety (for example, a fluorescent protein) from the construct provide a high level of specificity. Prior art methods, however, lacked the sensitivity necessary for important applications of such assays, for example environmental testing. This is particularly important considering the potential use of *botulinum* toxins as bioweapons.

Unless the context dictates the contrary, all ranges set forth herein should be interpreted as being inclusive of their endpoints, and open-ended ranges should be interpreted to include only commercially practical values. Similarly, all lists of values should be considered as inclusive of intermediate values unless the context indicates the contrary.

Cell-based assays require a rigidly controlled environment, utilizing physiological ion concentrations, osmolarity (i.e. 250-270 mOsm), and temperatures held at physiological level. Surprisingly, the inventors have found that reducing the sodium ion concentration of the culture media provides a dramatic increase in the sensitivity of some cell-based BoNT assays. The effect is not seen with potassium ions, is not a result of changes in osmolarity of the cell culture media, and is not observed with certain types of *botulinum* toxins. The inventors have also found that elevating the temperature at which the assay is performed by up to 4° C. results in a dramatic increase in the sensitivity of such an assay without impacting cell viability over the course of the assay. Similarly, decreasing the osmolarity of the cell media also resulted in an increase in sensitivity. These methods can be adopted without the need for specialized equipment, and the increased sensitivity realized broadens the range of applications for these highly specific *botulinum* toxin assays.

Methods of the inventive concept provide a transfected cell, which in turn produces a construct or fusion protein. With respect to the transfected cells expressing the hybrid protein it is generally preferred that the cell is stably transfected. Nevertheless, transient transfection is also contemplated. It is still further typically preferred that the transfected cell is a neuronal cell. However, numerous other non-neuronal cells (including mammalian cells, insect cells, yeast, bacteria, and artificial cells) are also contemplated herein. Most typically, the cells will constitutively express the hybrid protein(s) are therefore under appropriate regulatory elements. In alternative aspects, the expression can also be induced.

Many choices of cell lines are suitable as the host cell for the present invention. Preferably, the cell is of a type in which the respective *botulinum* toxin (BoNT) exhibits its toxic activities. In other words, the cells preferably display suitable cell surface receptors, or otherwise allow the toxin to be translocated into the cell sufficiently efficiently, and allow the toxin to cleave the suitable substrate polypeptide. Specific examples include primary cultured neurons (e.g., cortical neurons, hippocampal neurons, spinal cord motor neurons, etc); PC12 cells or cell lines derived from PC12 cells; primary cultured chromaffin cells; cultured neuroblastoma cell lines (such as murine cholinergic Neuro2A cell line), human adrenergic SK-N-SH cell lines, NS-26 cell lines, and stem cells (see e.g. Foster and Stringer (1999), Genetic Regulatory Elements Introduced Into Neural Stem and Progenitor Cell Populations, Brain Pathology 9: 547-567). Similarly, neuroendocrine and neuroendocrine-derived cell lines can be used. It should be appreciated, however, that in the instance of recombinant or mutated BoNTs that are directed towards non-neuronal cell types, that host cells can be selected from cell lines with the corresponding specificity.

Constructs or fusion proteins of the inventive concept can include a reporter-containing portion and a cleavage site. The cleavage site can act as a substrate for the protease activity associated with a *botulinum* toxin light chain. Such transfected cells can demonstrate stable transformation or transient transformation. Cleavage of the cleavage site releases at least a portion of the reporter-containing portion from a remainder of the construct. The reporter region can include an observable reporting group or tag, such as a fluorophore which provides an observable fluorescence. Suitable fluorophores include fluorescent dyes, and can include fluorescent proteins such as Green Fluorescent Protein (GFP), Cyan Fluorescent Protein (CFP), Yellow Fluorescent Protein (YFP), Citrine, Venus, YPet, mStrawberry, and/or mCherry protein. In some embodiments the hybrid protein can include multiple fluorophores, for example a second fluorophore. Such a second fluorophore can be located within the reporter region or at a distal location. For example, the fluorophore of the reporter region (i.e. the first fluorophore) can be located proximate to one terminus of the hybrid protein while the second fluorophore can be located proximate to a different terminus of the hybrid protein. Alternatively, both the first fluorophore and the second fluorophore may be within the reporter region. Depending upon the nature of the detection, the first fluorophore and the second fluorophore can be the same fluorophore species, or can be different fluorophore species. For example, in an assay system utilizing FRET detection the first fluorophore and the second fluorophore can be different fluorophore species.

In a preferred embodiment of the inventive concept, the reporter region includes one or more fluorophores of the same species, which can be arranged so that homo-FRET does not occur to a significant degree (i.e. less than 5% Förster resonance energy transfer). In other embodiments the construct can include fluorophores of different species, which can be arranged so that FRET does not occur to a significant degree (i.e. less than 5% Förster resonance energy transfer). This can be accomplished, for example, by placing the fluorophores at or near different termini of the construct. In such embodiments the emission spectra of a first fluorophore can overlap with the excitation spectra of a second fluorophore without significant (i.e. less than 5%) Förster resonance energy transfer, however fluorescence emission of the first fluorophore is not significantly decreased (i.e. less than 5%) via quenching and fluorescence emission of the second fluorophore is not significantly (i.e. more than 5%) increased via such energy transfer. In other embodiments of the inventive concept the construct can include a first fluorophore with an emission spectrum that overlaps the excitation spectrum of a second fluorophore, with position of the fluorophores within the construct arranged such that significant (i.e. >5% Förster resonance energy transfer) occurs between the fluorophores. Fluorescence from a construct of the inventive concept can be detected by any means suitable for the configuration of the construct, for example including direct excitation and emission from each fluorescent species, FRET, and fluorescence anisotropy. In a preferred embodiment, a conventional microwell plate fluorometer configured for direct excitation and emission detection from each fluorophore species can be used.

Green fluorescent protein and its mutations, which fluoresce without the need for additional cofactors or substrates, are particularly suitable for use with constructs of the inventive concept. For example, Yellow Fluorescent Protein (YFP) is a mutation of the Green Fluorescent Protein, derived from *Aequorea victoria*, and has an excitation peak at 514 nm and an emission peak at 527 nm. In addition to YFP, it is also contemplated to use related Citrine, Venus, and YPet proteins can be used in the reporter-containing portion. These mutations have reduced chloride sensitivity, faster maturation, and increased brightness (product of the extinction coefficient and quantum yield) relative to GFP. Of course, any of the fluorescent proteins mentioned herein can be modified to include specific characteristics (e.g., spectral) or be truncated to a specific size. It is also contemplated that the reporter containing portion includes reporters other than fluorescent proteins (e.g., a phosphorescent compound, a luminescent compound, a chromophore, an enzyme, etc.).

In some embodiments of the inventive concept the detection signal is characterized prior to exposure of the transfected cells to the *botulinum* toxin (BoNT), to provide a baseline signal. This baseline signal can serve as a basis for comparison to an assay signal obtained following exposure of the transfected cells to *botulinum* toxin, and can serve to normalize such an assay signal to at least partially correct for variations in cell number, density, and/or shape between different test sites. For example, the use of a ratio between a post-exposure signal and the baseline signal can serve to normalize fluorescence intensity between assays performed in different wells of a microwell plate, thereby reducing the variation between like measurements. Sensitivity can be assessed by preparing a series of such assays utilizing different concentrations of *botulinum* toxin to generate a dose/response curve, which is typically sigmoidal. Sensitivity can be quantified by determining the concentration of *botulinum* toxin that generates a response that correlates to a defined portion of the dose response curve. For example, a *botulinum* concentration that correlates with the midpoint or half-maximal value of the dose/response curve (typically reported as the EC50) can be used as a basis for comparing sensitivity in such assays.

Many different methods can be used to measure sensitivity to *botulinum* toxin using a cell-based assay. In one embodiment, an emission ratio of a first fluorescent protein and a second fluorescent protein that do not form a FRET pair (i.e. demonstrate less than about 5% energy transfer via FRET) can be measured after exposing the transfected cell to *botulinum* toxin. In such an embodiment, prior to exposure of the hybrid to *Botulinum* toxin, the construct exhibits a baseline signal, and the first fluorescent protein emission and the second fluorescent emission are separately measured. After exposure to *botulinum* toxin, the reporter-containing portion comprising the first fluorescent protein is cleaved by the *botulinum* toxin, and the cleaved reporter-containing portion is subsequently degraded by proteolysis. In such an example the emission intensity of the first fluorescent protein is decreased, while an emission intensity of the second fluorescent protein remains essentially the same. The emission measured from this second fluorescent protein is therefore a function of cell number, density, distribution, and so on, and is not a function of the concentration of *botulinum* toxin. As such, the emission from the second fluorescent protein can be used to normalize the emission measured from a fluorophore of the reporter region (in this instance the first fluorescent protein), for example by using an emission ratio. It should be appreciated that such an emission ratio is ineffective for data normalization in constructs in which the fluorophores are arranged to perform FRET, as the emissions from both fluorophores would change on cleavage of such a construct. The emission ratio (first fluorescent protein emission/second fluorescent protein emission) is decreased when the construct interacts with *botulinum* toxin. An example of a suitable construct in such an embodiment is one that includes Cyan Fluorescent Protein (CFP) outside of the reporter region and in which the reporter region includes Yellow Fluorescent Protein (YFP), configured such that the CFP and YFP do not form a FRET pair. Data related to the degree of YFP degradation (i.e. directly, separately excited YFP emissions and CFP emissions) following exposure to a *botulinum* toxin can be collected from a cell expressing such a construct. Those emissions can be background subtracted and the YFP emission divided by the CFP emission to control for cell density and reporter expression in the individual cells.

*Botulinum* toxin responsive emission from a fluorophore of a reporter region or an emission ratio can be used to generate a dose response curve that is useful in quantifying *botulinum* toxin in a sample and/or to determine sensitivity of an assay to *botulinum* toxin. Such sensitivity is frequently expressed as a concentration of the BoNT corresponding to a characteristic portion of the dose/response curve. For example, a BoNT concentration corresponding to the midpoint of such a curve is referred to as an $EC_{50}$.

In one embodiment of the inventive concept, the transfected cells are exposed to the *botulinum* toxin at a temperature that is elevated relative to that at which cell culture and such assays are normally performed (i.e. 37.0° C.). It should be appreciated that such temperatures are generally considered non-optimal for cell survival, and that their use is counterintuitive in assays that rely on the use of viable cells. In a preferred embodiment the temperature at which the transfected cells are exposed to *botulinum* toxin is such that the sensitivity is increased at least two-fold (i.e. by a factor of 2) relative to an assay performed at 37.0° C. (i.e. the EC50 of the assay performed at the elevated temperature is less than half of the EC50 of the assay performed at 37.0° C.). Surprisingly, the inventors have found that such a sensitivity enhancement occurs within a relatively narrow range of temperatures. In some embodiments of the inventive concept the transfected cells are exposed to the *botulinum* toxin at 38.0° C. to 41.0° C. In other embodiments of the inventive concept the transfected cells are exposed to the *botulinum* toxin at a temperature between 38.5° C. and 39.5° C.

Alternatively, the transfected cells of the inventive concept can be maintained at temperatures greater than 37.0° C. prior to exposure to the *botulinum* toxin, for example 38.0° C. to 41.0° C. or 38.5° C. and 39.5° C. In such embodiments, exposure of the transfected cells to *botulinum* toxin can be performed at 37.0° C. Alternatively, in some embodiments transfected cells can be exposed to temperatures greater than 37.0° C. (for example, 38.0° C. to 41.0° C. or 38.5° C. and 39.5° C.) both prior to and during exposure to *botulinum* toxin. In still other embodiments the temperature of the transfected cells can be ramped during the performance of the assay. For example, the temperature of the transfected cells can start at 37.0° C. at the point of introduction of the *botulinum* toxin and then increased (for example, to 41.0° C.) as the assay progresses. Alternatively, in some embodiments the temperature of transfected cells can start at an elevated temperature (for example, 41.0° C.) at the point of introduction of the *botulinum* toxin and be decreased to 37.0° C. during the course of the assay.

In embodiments of the inventive concept, a cell-based assay detecting the presence of *botulinum* toxin can have an increase of at least two fold in sensitivity to *botulinum* toxin with a change of conditions (e.g., temperature, osmolarity, extracellular ion concentration, etc.). In one preferred embodiment, the sensitivity to *botulinum* toxin is increased at least three fold when the transfected cell is exposed to *botulinum* toxin at a higher temperature than 37.0° C., within a range of 38° C. to 41° C., or within a range of 38.5° C. to 39.5° C. compared to sensitivity to *botulinum* toxin at 37.0° C. In another embodiment the sensitivity is increased at least five fold when the transfected cell is exposed to *botulinum* toxin at a higher temperature than 37.0° C., within a range of 38° C. to 41° C., or within a range of 38.5° C. to 39.5° C. compared to sensitivity to *botulinum* toxin at 37.0° C. In still other embodiments the sensitivity is increased at least ten fold when the transfected cell is exposed to *botulinum* toxin at a higher temperature than 37.0° C., within a range of 38° C. to 41° C., or within a range of 38.5° C. to 39.5° C. compared to sensitivity to *botulinum* toxin at 37.0° C.

It is also thought that reduced osmolarity of a cell media in which the transfected cell is exposed to BoNT can also enhance sensitivity to BoNT. Without wishing to be bound by theory, the inventors believe that reduced extracellular osmolarity can result in a modulation of cellular activity (e.g. neuronal excitability). Especially, in neuronal cells, reduced osmolarity enhances synaptic transmission and neuronal excitability, which increases the endocytosis rate. Thus, it is contemplated that a reduction in osmolarity of a cell media in which the transfected cell is exposed to *botulinum* toxin, for example to a range between 220 milliOsm and 260 milliOsm may confer an increase in sensitivity to *botulinum* toxin. It should be appreciated that such a modification is counterintuitive, as such conditions can adversely affect cell viability. Furthermore, it is also contemplated that reduced osmolarity of the cell media can enhance, for example in a synergistic fashion, an increased sensitivity to *botulinum* toxin that results from a higher temperature than 37.0° C.

In another embodiment, increased sensitivity to *botulinum* toxin can be achieved by decreasing the concentration of specific extracellular ions, for example free (i.e. uncomplexed or non-chelated) calcium. When extracellular calcium concentration falls below normal physiological level, the transfected cell can be progressively more excitable. Similar to reduced osmolarity, increased cell excitability can enhance endocytosis rate and thus enhance the internalization of an applied *botulinum* toxin. Thus, it is also contemplated that reducing calcium concentration below the physiological level (1.0-1.5 mM) may confer a similar increase in sensitivity to *botulinum* toxin. Similarly, addition of calcium chelators (e.g., ethylenediaminetetraacetic acid (EDTA), ethyleneglycoltetraacetic acid (EGTA), 1,2-bis-(2-aminophenoxy)ethane-N,N,N',N'-tetraacetic acid tetra(acetoxymethyl) ester (BAPTA/AM), and other organic acids) to the cell media may confer similar increases in sensitivity to *botulinum* toxin.

In still another embodiment of the inventive concept, an increase in the sensitivity of a cell-based assay for a *botulinum* toxin increased when the sodium ion concentration of the cell culture media utilized during the performance of the assay is reduced. For example, cell culture media can be prepared with sodium salts, for example NaCl and/or $NaHCO_3$, omitted from the formulation. Such cell culture media can have final sodium ion concentration of less than about 70 mM, about 50 mM, about 40 mM, about 30 mM, about 25 mM, or about 20 mM. In a preferred embodiment of the inventive concept the cell culture media used to perform a cell-based *botulinum* toxin assay is less than or equal to about 20 mM.

In performance of a cell-based assay, cells expressing a *botulinum*-sensitive construct as described above can be pre-incubated with a low sodium ion content culture media prior to exposure to the *botulinum* toxin, then contacted with a low sodium ion content culture media containing *botulinum* toxin (for example, from an added sample). In preferred embodiments of the invention, the cells are not exposed to a low sodium ion content culture medium prior to exposure of the cells beyond a brief (i.e. several minute) exchange or wash with low sodium ion content culture media prior to contact with the *botulinum* toxin.

In some embodiments of the inventive concept sodium ions in the cell culture media can be replaced by other ions that do not show the sodium ion effect (for example, potassium ions) or by other osmolarity modifying agents (for example, triethylamine N-oxide) to retain the physiological osmolarity of the cell culture media while still providing the sensitivity enhancement realized by the reduction in sodium ion concentration.

It should be appreciated that elevated temperature, reduced media osmolarity, reduced extracellular concentration of specific ions (for example, sodium ions), and additional protein can be combined, and that such combinations can exert a synergistic effect. For example, the inventors have surprisingly found that elevated temperature during exposure of the transfected cells to *botulinum* toxin and the use of media with reduced osmolarity has a synergistic effect on the improvement in sensitivity of a cell based assay.

A number of serotypes of *botulinum* toxin (BoNT) with different substrate specificities and specific cleavage sites have been identified, including BoNT/A, BoNT/B, BoNT/C, BoNT/D, BoNT/D, BoNT/E, BoNT/F, BoNT/G, and a proposed BoNT/H. In some embodiments of the inventive concept, a sensitivity enhancing method can be selective for a specific species of BoNT. For example, the use of a low sodium content cell culture medium can result in an enhanced sensitivity for a cell-based assay for BoNT/A, but have little effect on the sensitivity of a cell-based assay BoNT/E. In some embodiments of the inventive concept this selective enhancement of the sensitivity to one or more BoNT species occurs when the same cell line expressing the same construct is used in characterizing multiple BoNT species.

It is contemplated that a construct of the inventive concept can be responsive (i.e. act as a substrate) for one or more of such BoNTs. Similarly, it is contemplated that transfected cells expressing hybrid reporter/cleavage site bearing proteins that can act as substrates for recombinant or modified BoNTs with altered specificity and BoNT serotypes and/or isoforms not yet identified will be responsive to the methods of the inventive concept. It is also contemplated that transfected cells expressing proteins with similar reporter and different cleavage site portions that are responsive to Tetanus neurotoxins (TeNTs) can show similar increases in sensitivity to the respective TeNT when methods of the inventive concept are applied.

In a preferred embodiment, temperatures higher than 37.0° C. significantly and cell culture media with low (i.e. less than about 70 mM) sodium ion concentration enhance the sensitivity of the BOCELL™ model cell line to botulinum neurotoxin type A (BoNT/A). Such a cell line is described in U.S. Provisional Patent Application No. 61/492,237 (filed Jun. 1, 2011) and is incorporated herein. All other extrinsic materials discussed herein are similarly incorporated by reference in their entirety.

BoNTs recognize the cleavage site and cleave the hybrid protein into the reporter-containing portion and the remainder of the hybrid protein. The cleavage site sequence of the present invention can advantageously comprise (a) a SNARE protein, motif, or mutein (or a cleavable portion of these). SNARE proteins are understood to include SNAP-25, synaptobrevin (VAMP), and syntaxin. "Muteins" of a protein should be interpreted herein as having at least 30% identity with a corresponding native protein, including for example compositions having at least 35%, 40%, 45%, 50%, 55%, 60%, 65%, 70%, 75%, 80%, 85%, 90%, 95% or 98% identity with the native protein. Variations from identity can comprise any or more of additions, deletions and substitutions. Contemplated muteins include fragments, truncates and fusion proteins.

Figure 1C:
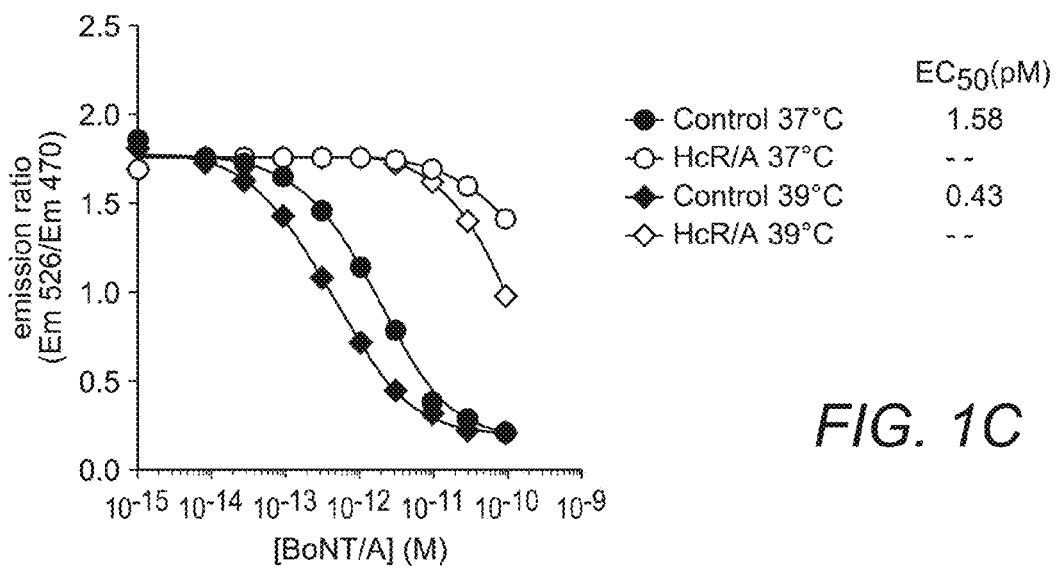

Without wishing to be bound by theory, the inventors believe that the observed increased sensitivity to botulinum toxin at higher temperatures could be a consequence of increased specific binding and endocytosis of botulinum toxin. In the cell-based assay, BoNT must be internalized to the cell cytoplasm via receptor-mediated endocytosis. It is therefore possible that anything that causes more BoNT to be internalized, and to interact with the cleavage site of hybrid proteins/constructs, would result in the transfected cell being more sensitive to BoNT. As shown FIG. 1A, which depicts dose/response curves obtained with botulinum toxin at different temperatures, relatively small changes in temperature produce a surprisingly large effect on the sensitivity of a Botulinum toxin assay (as determined by EC50). FIG. 1B shows the result of similar studies performed using intact Botulinum toxin (i.e. holotoxin) and the botulinum toxin light chain, which has protease activity capable of cleaving the cell's reporting construct but does not have receptor-binding activity. The lack of change in the emission ratio of the construct noted at conventional and elevated temperatures when the cells are exposed to the light chain indicates that temperature effects are not a result of generally enhanced endocytosis and are a result of receptor-mediated processes. This is supported by the data shown in FIG. 1C, which shows the effects of different temperatures on transfected cells exposed to botulinum toxin in the presence of absence of botulinum toxin heavy chain, which lacks the ability to cleave the reporting construct but can occupy toxin-specific receptor sites. FIG. 1C shows that the Botulinum toxin heavy chain is effective in blocking the effects of the holotoxin but less effective at the elevated temperature, indicating that the temperature effect of cell-based assay sensitivity may be a receptor-mediated process.

Increased expression of botulinum toxin receptor proteins on the transfected cell's surface may results in enhanced endocytosis of botulinum toxin. For example, botulinum toxin A, D and E are internalized to cell cytoplasm via interaction with synaptic vesicle proteins (SV2) expressed on cell surface. Thus, it is also contemplated that co-expression of SV2 protein in the transfected cell may infer similar increase in sensitivity to botulinum toxin.

Increased activity of endogenous stress response proteins, including Heat Shock Protein 70 (HSP70) and Heat Shock Protein 90 (HSP90), at the higher temperature can potentially induce enhanced sensitivity to botulinum toxin. Both HSP70 and HSP 90 are activated at higher temperatures than physiological temperature range (between 35.0-37.0° C.), and enhance proteolysis activity of the cell. Without wishing to be bound by theory, it is contemplated that increased activity of HSP70 or HSP90 can facilitate breakdown of the reporter-containing portion of the hybrid protein.

Still further, a conformational change of the hybrid protein at the higher temperature, by which the baseline FRET signal can be augmented, can induce enhanced sensitivity to botulinum toxin. HSP70 functions to aid proper folding of proteins, and increased activity of HSP70 may induce a conformational change of the hybrid protein. Therefore, it is also contemplated that treatment of HSP70 activator (e.g., YM1 (2-((Z)-((E)-3-ethyl-5-(3-methylbenzo[d]thiazol-2(3H)-ylidene)-4-oxothiazolidin-2-ylidene)methyl)-1-methylpyridin-1-ium chloride, 2-[3-Ethyl-5-(3-methyl-3H-benzothiazol-2-ylidene)-4-oxo-thiazolidin-2-ylidenemethyl]-1-methyl-pyridinium chloride)) to the transfected cell may infer similar increase in sensitivity to botulinum toxin.

It is further contemplated that various conditions described above can be combined to render further enhanced sensitivity to BoNT in the cell based assay. For example, reduced osmotic strength and reduced sodium concentration in the media can be combined to provide further sensitivity enhancements. It is contemplated that such combinations can produce synergistic effects.

Still another embodiment of the inventive concept is a kit that includes preparations that include sensitivity enhancing media as described above and one or more botulinum toxins at different concentrations. For example, such a kit can include a set of preparations comprising a sensitivity enhancing media, wherein each member of the set additionally includes a different concentration of botulinum toxin. Such sensitivity enhancing media can be as described above, for example media containing sodium at less than or equal to 50 mM sodium. Such sensitivity enhancing media can have physiological or less than physiological osmotic strength.

In such a kit the preparations can be prepared such that they represent a series of botulinum toxin concentrations suitable for use as a dose/response curve. Such a dose/response curve can, in turn, be used for calibrating a cell-based botulinum toxin assay to produce a characteristic response. Alternatively, such a kit can contain a limited number of such preparations (for example one, two, or three preparations) that may not be suitable for producing a dose/response curve but that can be used to verify that a cell-based botulinum assay is producing results consistent with those of a complete dose/response or calibration curve that is stored in computer memory. Optionally, such a kit can include a preparation that does not include botulinum toxin, for use as a diluents, control, blank sample, and/or zero standard. In an alternative embodiment, such a kit can include a supply of media (for example, a sensitivity enhancing media without botulinum toxin) and a supply of botulinum toxin stock. Such a supply of sensitivity enhancing media can be provided as a bulk supply or, preferably, as a series of aliquots in individual containers containing characterized volumes. It should be appreciated that in such an embodiment the components can be provided as separate components in order to accommodate different stabilizing conditions (for example, different temperatures, buffer conditions, stabilizing reagents, etc.). In such an embodiment, directions are supplied to a user for addition of the botulinum toxin stock to the incomplete preparations in order to generate complete preparations that can be used as described above.

EXAMPLES

Temperature Effects.

Cell based assays to detect botulinum toxin (BOCELL™ assay) were performed at 35.0° C., 37.0° C., and 39.0° C. (Trials 1 and 2), and at 37° C., 39° C., and 41° C. (Trial 3) using botulinum toxin/A holotoxin at concentrations ranging between $10^{-15}$ M to $10^{-9}$ M. The transfected cells were exposed to one of the three temperatures while being exposed to the botulinum toxin. Dose/response curves were generated by characterizing emission ratios (YFP/CFP) at each concentration and plotting them as a function of botulinum toxin/A concentration. As shown in FIG. 1A, by increasing the temperature used in the assay from 37° C. to 39.0° C. or 41° C. the sensitivity to botulinum toxin (measured as $EC_{50}$ value) is enhanced more than 5 fold.

In the studies depicted in FIG. 1B the transfected cells were treated with either botulinum toxin/A holotoxin or botulinum toxin/A light chain and incubated at either 37.0° C. or 39.0° C. Botulinum toxin/A light chain retains the ability to cleave the detection construct expressed by the cells, but lacks the ability to bind to the specific cell surface receptor utilized by the intact holotoxin. In these studies botulinum toxin/A light chain does not cleave the cleavage site containing portion of the reporting construct, even at high concentrations. This indicates that intact BoNT/A undergoes receptor-mediated toxin uptake process and activation within the cell at both 37.0° C. and 39.0° C., and that the enhanced sensitivity is a receptor-mediated process.

Confirmation of this is found in the studies shown in FIG. 1C. Transfected cells were pre-treated with botulinum toxin/A heavy chain or the equivalent vehicle prior to addition of botulinum toxin/A holotoxin. Botulinum toxin/A heavy chain lacks toxicity (i.e. proteoplytic activity) and cannot cleave the detecting construct expressed by the cell, but binds to an occupies the specific receptor bound by the holoxin. Preincubation of the transfected cells with the heavy chain, which comprises the receptor binding domain, botulinum toxin/A holotoxin uptake and reporter cleavage at both 37.0° C. and 39.0° C., indicating a requirement for receptor-mediated endocytosis of BoNT/A holotoxin for reporter cleavage at elevated temperatures.

Figure 2:
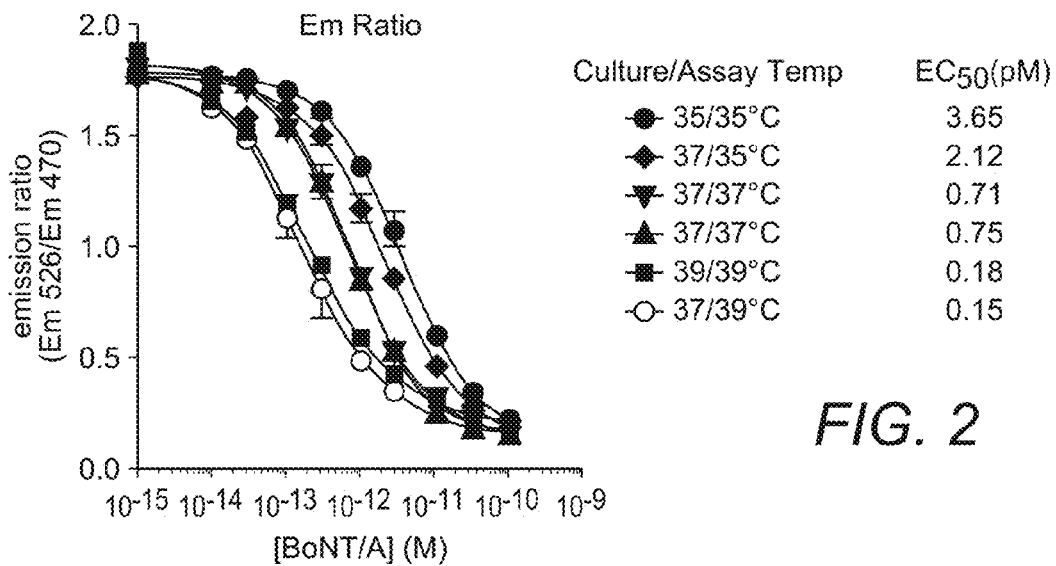
FIG. 2 shows the response of transfected cells to *botulinum* toxin at different pre-toxin exposure (i.e. culture) temperatures and toxin exposure (i.e. assay) temperatures.

The effects of pre-treatment of cells using elevated temperatures is shown in FIG. 2. Cell based assays to detect BoNT (BoCell™ assay) were performed at 35.0° C., 37.0° C., and 39.0° C., using botulinum toxin/A holotoxin at concentrations ranging between $10^{-15}$ M to $10^{-9}$ M. The transfected cells were exposed to one of these three temperatures before being exposed to botulinum toxin, then exposed to the same or a different temperature among the three temperatures during exposure. The sensitivity to botulinum toxin, characterized as a reduced EC50 value, was enhanced in transfected cells exposed to botulinum toxin at 39.0° C. Sensitivity to botulinum toxin at 39.0° C. was at least 3 fold greater than the sensitivity to botulinum toxin at 37.0° C., and at least more than 10 fold compared to sensitivity to Botulinum toxin at 35.0° C.

Figure 3A:
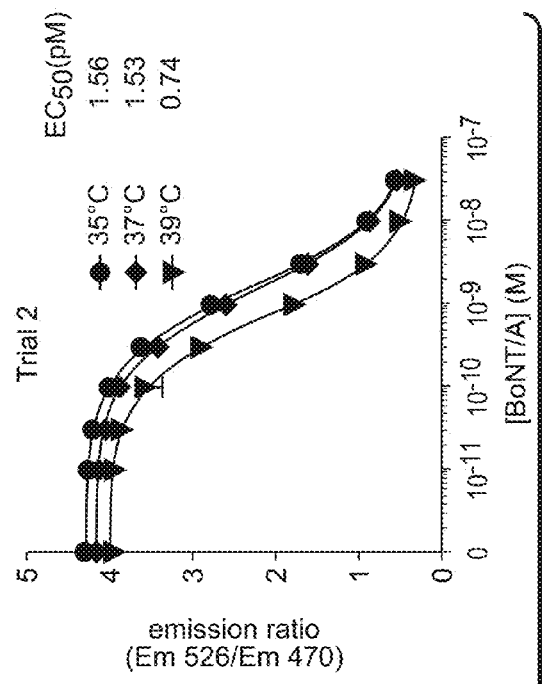
FIGS. 3A and 3B show the effect of media ionic strength on the response of transfected cells to *botulinum* toxins at different temperatures.
Figure 3A:
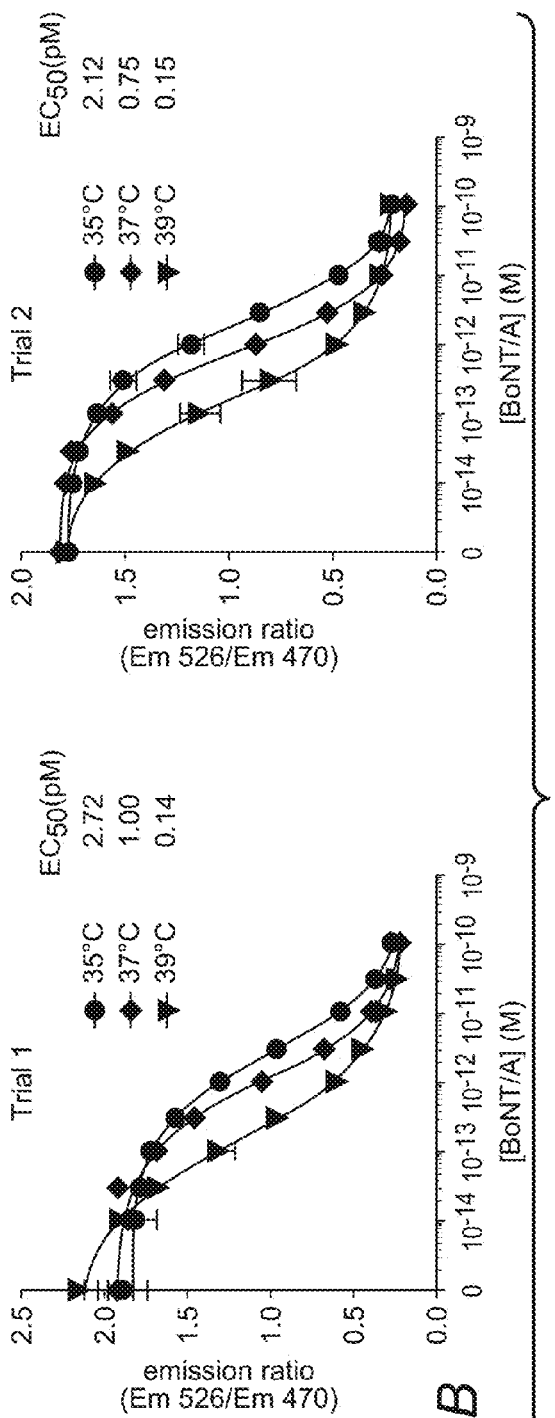
Figure 3B:
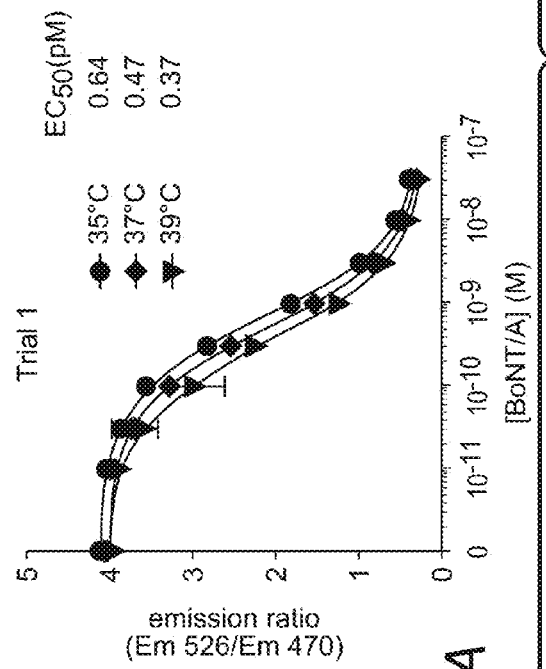

The effects of elevated temperature combined with reduced osmolarity are shown in FIGS. 3A and 3B. Cell based assays to detect botulinum toxin (BOCELL™ assay) were performed at 35.0° C., 37.0° C., and 39.0° C., where the transfected cells were exposed to Botulinum toxin in a cell media with an osmolarity of approximately 270 mOsm (i.e. normal osmolarity). Consistent with previous observations and as shown in FIG. 3A, the observed sensitivity to botulinum toxin at 39.0° C. is increased up to approximately 2 fold compared to sensitivity at 37.0° C. Similar studies were performed using an otherwise identical cell culture media with an osmolarity of less than 250 mOSm. The results are shown in FIG. 3B. Sensitivity to botulinum toxin at 39.0° C. is increased up to approximately 7 fold compared to sensitivity to botulinum toxin at 37.0° C. Surprisingly, reduced osmolarity had relatively little effect at 37° C. and actually decreased sensitivity at 35° C., indicating a synergistic interaction between reduced osmolarity and elevated temperature.

Figures 4A, 4B:
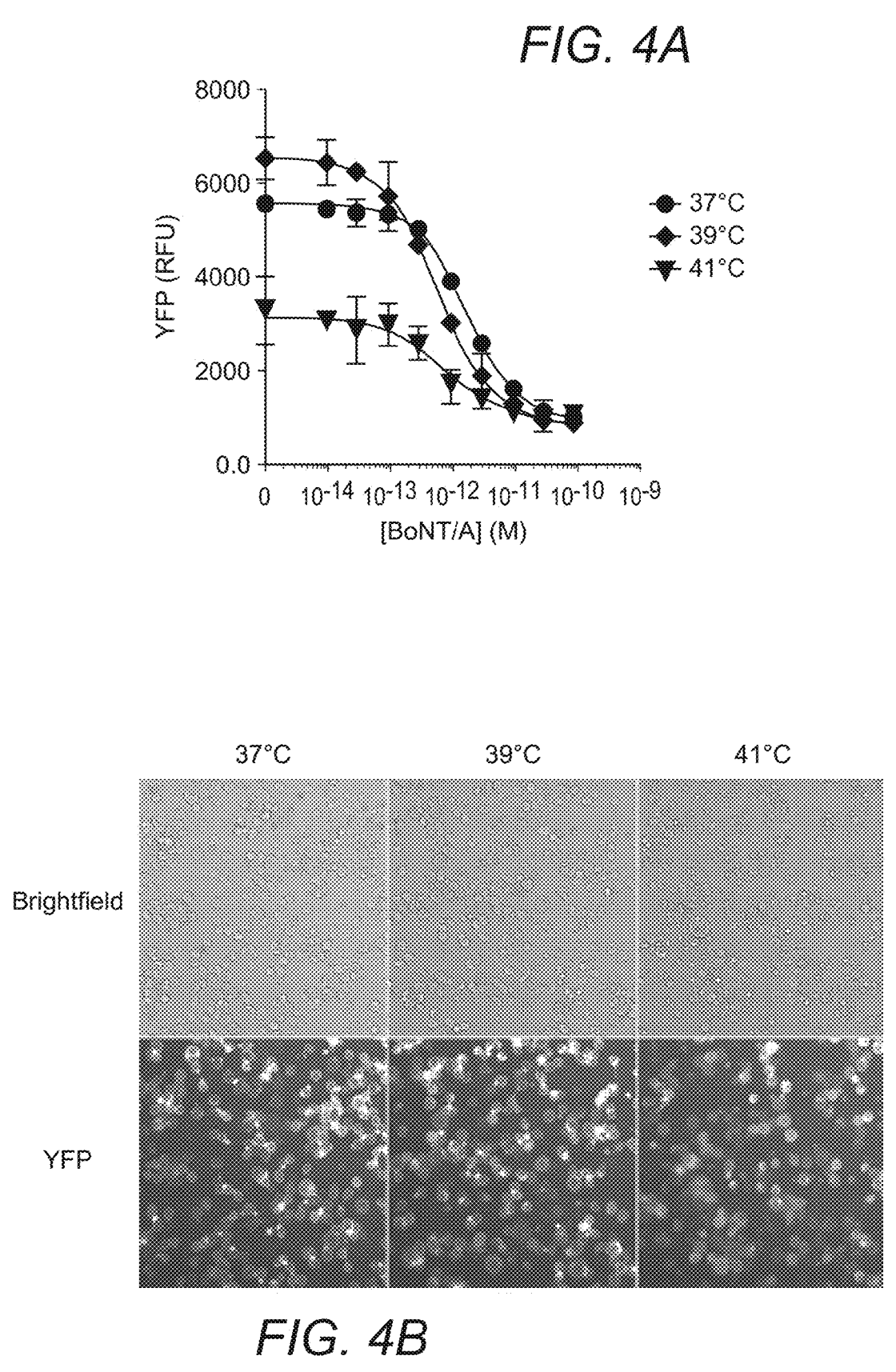

As shown in FIG. 4A, the sensitivity enhancing effect of elevated temperature occurs within a narrow range of temperatures. Fluorescence data from the cell-based assays performed at elevated temperatures show a loss of signal from a fluorescent protein of the construct at 41.0° C. when compared to lower temperatures, which can be indicative of poor cell health. Images of transfected cells under brightfield and fluorescence microscopy confirm poor cell health at 41.0° C., as shown in FIG. 4B. The transfected cells show poor morphology at 41.0° C. (brightfield) and an overall decrease and diffusion of the reporter protein of the construct (YFP) at 41.0° C.

Figure 5:
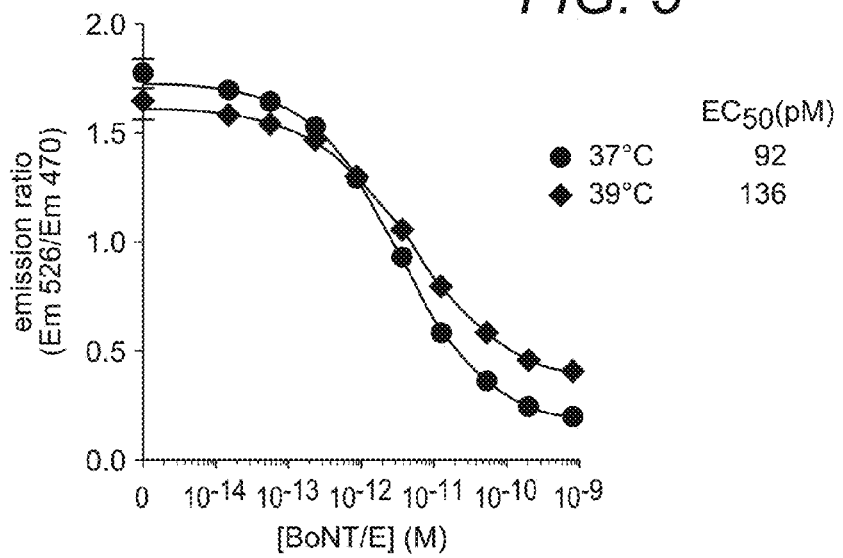
FIG. 5 shows the effect of increased temperature on a cell-based assay for BoNT/E toxin.

Selectivity of the temperature effect is shown in FIG. 5. The temperature studies shown above depict the results from using BoNT/A and transformed cells expressing a construct that can be cleaved by BoNT/A. BoNT/A and BoNT/E both cleave sites within SNAP-25, and a reporting construct incorporating SNAP-25 or a portion of SNAP-25 that includes these cleavage sites can potentially be used in the detection of either BoNT/A and BoNT/E. FIG. 5 shows the results BoNT/E cell-based assays utilizing the BOCELL™ cells described above. Surprisingly, despite utilizing the same cells and cell culture media, the use of elevated temperature within the range found to be effective for enhancement of BoNT/A assay sensitivity (i.e. 39° C.) resulted in a decrease in sensitivity for BoNT/E (shown as an elevated EC50 value). This indicates that the temperature effect may be selective for specific BoNTs.

Sodium Ion Effects.

Results of studies showing the effect of reduced sodium chloride (NaCl) concentration are shown in FIG. 6A. A custom basal cell culture media was prepared that contained no added NaCl. Variations of this custom basal media were prepared by adding NaCl at various concentrations and cell-based assays for botulinum toxin/A were performed using BOCELL cells. Cells were incubated for 3 hours prior to the application of media containing BoNT/A at the indicated concentrations. Fluorescence of the fluorophores (i.e. YFP and CFP) of the construct expressed by the cells was characterized 48 hours after contacting the cells with BoNT/A. The highest concentration of NaCl (48 mM) represents the NaCl content of the conventional basal cell culture media. As shown, reduction of the NaCl concentration produces a dramatic enhancement of sensitivity (indicated by reduced EC50 values), finally resulting in a nearly 50-fold increase in sensitivity in the absence of added NaCl.

Figure 6B:
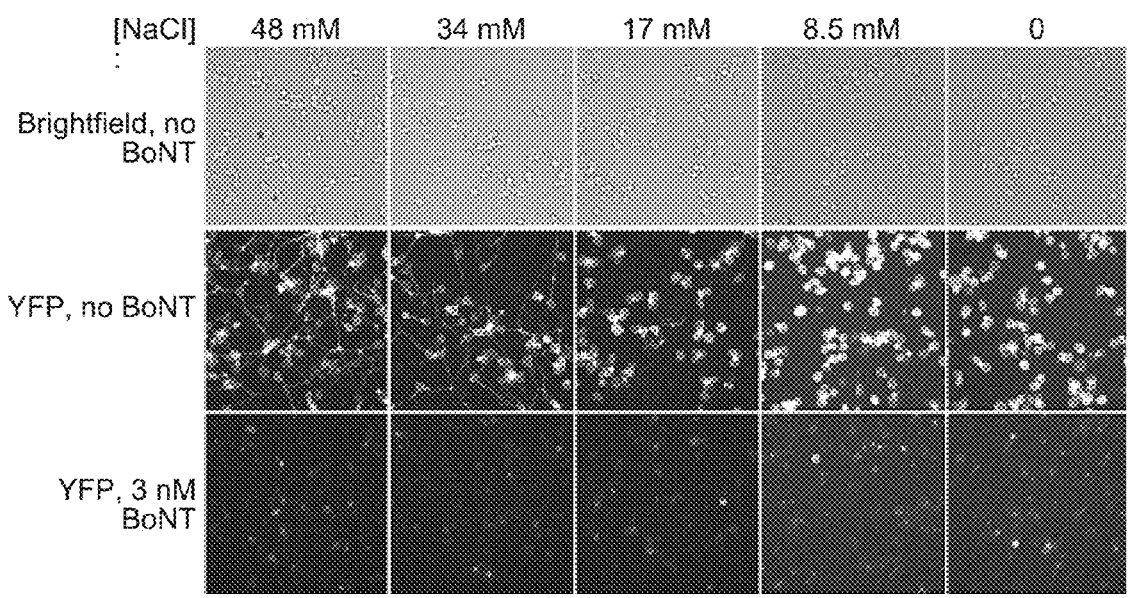

The effects of reduced NaCl concentration on cell morphology (brightfield) in the absence of BoNT/A and the distribution of the construct within the transformed cells (YFP) in the absence and presence of BoNT/A after 48 hours are shown in FIG. 6B. There is no evidence of changes in morphology or distribution of the construct at various NaCl concentrations in the cell culture media.

Figure 7:
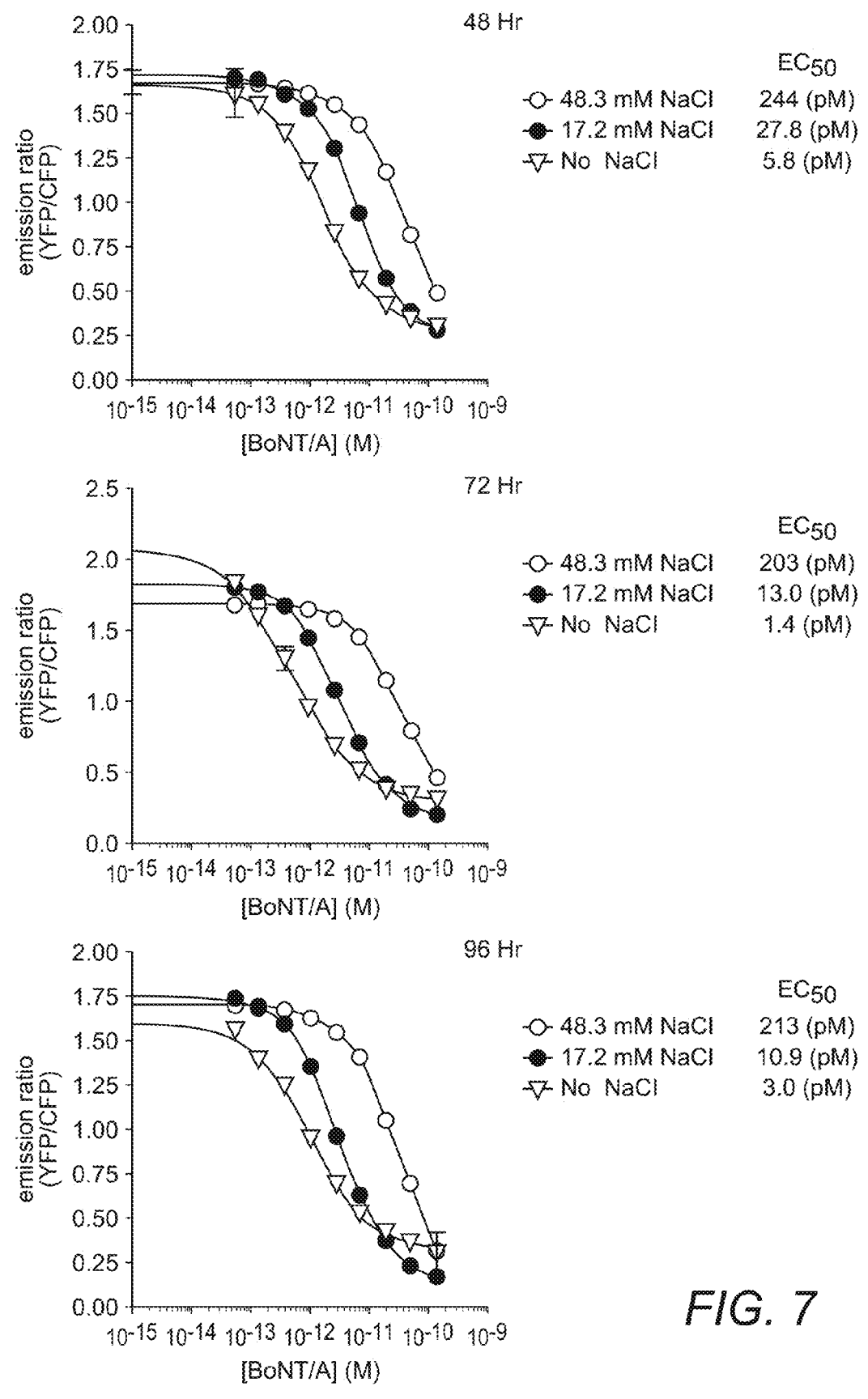

The impact of varying NaCl content of the cell culture media is shown in FIG. 7. A custom basal cell culture media was prepared that contained no added NaCl. Variations of this custom basal media were prepared by adding NaCl at various concentrations and cell-based assays for *botulinum* toxin/A were performed using BOCELL cells. Basal media containing 48.3 mM NaCl represents the NaCl concentration of the conventional basal media. Cells were incubated with media containing BoNT/A at the indicated concentrations for 48, 72, and 96 hours. Fluorescence of the fluorophores (i.e. YFP and CFP) of the construct expressed by the cells was characterized 48 hours after contacting the cells with BoNT/A. The highest concentration of NaCl (48 mM) represents the conventional NaCl content of the basal cell culture media. As shown, the concentration of NaCl has little effect on the timing of the cell-based assay.

Figure 8A:
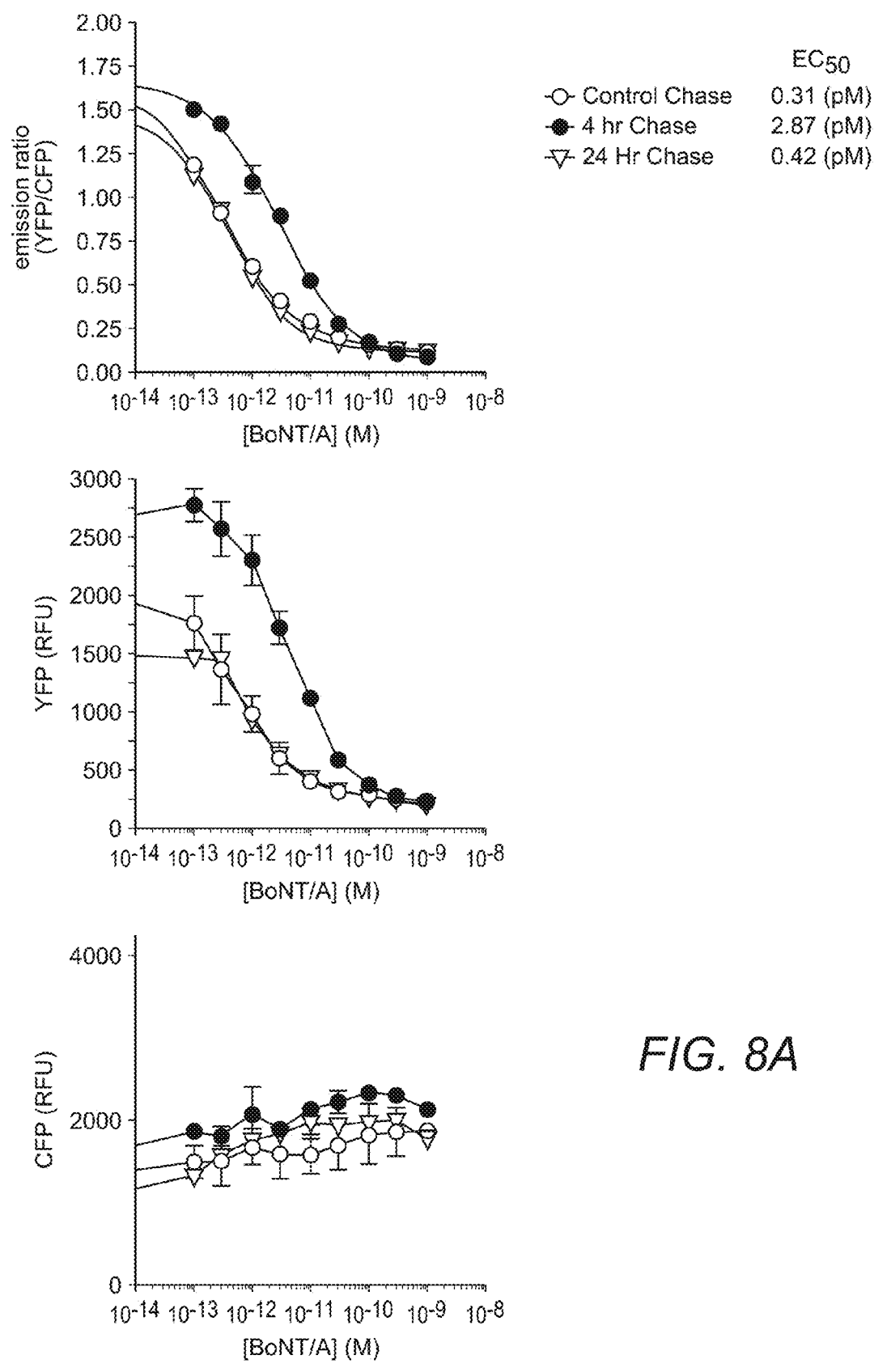
Figure 8B:
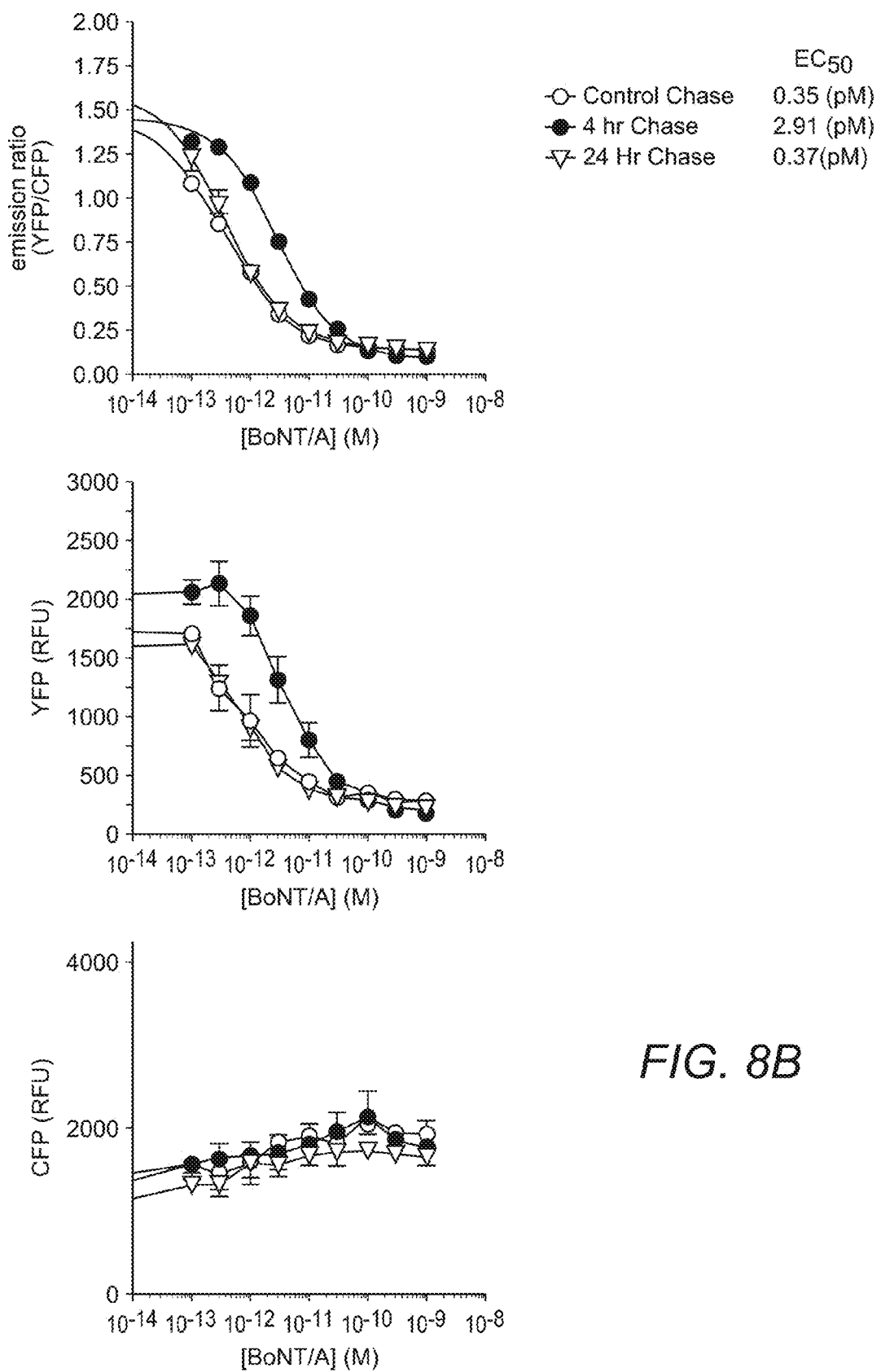

FIGS. 8A, 8B, and 8C show typical results of studies of the effects of the timing of the introduction of low sodium content media on the sensitivity of cell-based BoNT assays. FIG. 8A shows the results of cells carrying appropriate reporting constructs incubated in a basal media with conventional sodium content prior to exposure (i.e. pre-incubation) to a concentration of BoNT/A in low sodium content basal media for either 4 hours or 24 hours. Following these time periods the cells were transferred to basal media with conventional sodium content that contained a corresponding concentration of BoNT/A, such that the total time spent exposed to BoNT/A was 48 hours. Cells were also exposed to BoNT/A in low sodium content basal media for the entire 48 hour period to provide control conditions. FIG. 8B shows typical results for similar studies performed using the low sodium content basal media for pre-incubation. It should be appreciated that the media used for pre-incubation of the cells had no discernible effect on the cells, indicating that pre-conditioning of the cells using low sodium content media is not necessary.

The effect of pre-incubation was also examined in the studies shown in FIG. 8C, which shows typical results. Cells were pre-incubated with a supplemented conventional sodium content media (Media A) or with a low sodium content custom media (Media B). Cells were then washed briefly with either an unsupplemented conventional sodium content media (Media C) or the low sodium content custom media prior to contact with BoNT. As shown, pre-incubation in low sodium content media is not necessary to generate the enhanced BoNT sensitivity.

Counterion Effects.

The sodium content of the cell culture media used in a cell-based BoNT assay of the inventive concept can be manipulated by adjusting the concentration of sodium salts other than NaCl. As shown in FIG. 9A, a reduction in the sodium bicarbonate ($NaHCO_3$) content of a basal media is also effective at increasing the sensitivity of a cell-based BoNT assay. As shown in FIG. 9B, just as with NaCl large improvements in sensitivity are observed over relatively small changes in sodium content.

Ionic Strength and Osmolarity Effects.

The effects of removal of sodium from the media used in a cell-based BoNT assay are not due to changes in ionic strength. FIG. 10 shows typical results from studies in which a series of custom media having conventional (i.e. 70%) and reduced (i.e. 25%) sodium content and in which sodium is replaced by potassium at the same concentrations. While the enhancement of sensitivity in a cell-based BoNT assay is evident on reduction of sodium concentration, a similar enhancement is not observed when sodium is replaced with potassium and the concentration subsequently reduced. As such the effect is independent of ionic strength and can be seen as ion-specific and/or ion-selective.

FIG. 11 shows the results of supplementing low sodium content media with nonionic substances to increase ionic strength. Cell based BoNT assays were performed in culture media containing 48 mM NaCl (70% Neurobasal, total [Na+]=53 mM), 0 mM NaCl (70% custom 0 mM NaCl, total [Na+]=19 mM), and 0 mM NaCl media supplemented with either sucrose or trimethylamine N-oxide (TMAO). Both sucrose and TMAO are commonly used to adjust osmolarity. The sensitivity enhancement produced by the reduction of sodium in the culture media remains despite adjusting the osmolarity to the equivalent of 48 mM NaCl. The effects of reduction in sodium content in the culture media utilized in cell-based BoNT assays is therefore independent of osmolarity.

Mechanistic Studies of Low Sodium Content Media.

There are a variety of mechanisms that may be involved in enhancement of the sensitivity of cell-based BoNT assays through the use of low sodium content culture media. FIG. 12A shows typical results obtained in studies directed towards blocking cell surface receptor-mediated uptake of BoNT by cells in low sodium content culture media. Such cells were treated with a recombinant heavy chain fragment of BoNT/A (HcR/A, at 1 µM) prior to exposure of the cells to the intact BoNT/A holotoxin. Such heavy chain fragments of BoNT/A bind to the same cell surface receptors as the holotoxin but lack proteolytic activity and cannot cleave the detecting construct. As shown, blocking these receptor sites effectively blocks the toxic effects of the BoNT/A holotoxin when applied in low sodium content culture media at all but high holotoxin concentrations.

The recombinant light chain fragment of BoNT/A (Lc/A) retains the proteolytic activity of the BoNT/A holotoxin, but lacks the ability to bind to the cell surface receptors utilized for internalization of the holotoxin. FIG. 12B shows typical results for a study on the internalization of the BoNT/A light chain by cells in low sodium content culture media. As shown Lc/A has minimal impact on these cells, indicating that nonspecific endocytosis is not a primary factor in the sensitivity enhancement seen with low sodium content media.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to a first and a second steps, the text should be interpreted to mean that the first and second steps can be practiced in any order, not that the claim requires both element should be present or two elements are in such order. Where the specification claims refers to at least one of something selected from the group consisting of A, B, C . . . and N, the text should be interpreted as requiring only one element from the group, not A plus N, or B plus N, etc. Similarly, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

What is claimed is:

1. A method of increasing the sensitivity of cell-based detection of a *botulinum* toxin, comprising:
   (i) providing a transfected cell that produces a construct comprising;
      (a) a first terminus comprising a reporter-containing portion, wherein the reporter-containing portion exhibits a signal; and,
      (b) a cleavage site that interacts with the *botulinum* toxin in a manner that produces a cleavage of the reporter-containing portion from a remainder of the construct;
   (ii) exposing the transfected cell to the *botulinum* toxin at a toxin exposure temperature of from 38° C. to 41° C., wherein sensitivity of the transfected cell's response to the *Botulinum* toxin at the toxin exposure temperature increases at least 2 fold compared to the transfected cell's sensitivity to the *botulinum* toxin at 37° C.;
   (iv) obtaining the signal from the reporter-containing portion.

2. The method of claim 1 wherein the transfected cell is selected from the group consisting of a neuronal cell, a neuroendocrine tumor cell, a hybrid cell, and a stem cell.

3. The method of claim 1 wherein the reporter-containing portion comprises a first fluorophore.

4. The method of claim 1 wherein the hybrid protein further comprises a second fluorophore.

5. The method of claim 4, wherein second fluorophore is located proximal to a second terminus of the hybrid protein.

6. The method of claim 4 wherein the first fluorophore and the second flurophore demonstrate ≤5% Förster resonance energy transfer.

7. The method of claim 1 wherein the temperature is between 38.5° C. and 39.5° C.

8. The method of claim 1, comprising the additional step of exposing the transfected cell to a pre-toxin temperature prior to exposure to the *botulinum* toxin.

9. The method of claim 1 wherein the temperature of the cell prior to exposure to the *botulinum* toxin is between 38.0° C. and 41.0° C.

10. The method of claim 1 wherein the temperature of the cell prior to exposure to the *botulinum* toxin is between 38.5° C. and 39.5° C.

11. The method of claim 1 wherein the sensitivity of the transfected cell's response to the *botulinum* toxin increases at least five fold.

12. The method of claim 1 wherein the increase in sensitivity of the transfected cell's response is selective for *botulinum* toxin A (BoNT/A).

* * * * *